(12) United States Patent
Kwon et al.

(10) Patent No.: US 9,888,903 B2
(45) Date of Patent: Feb. 13, 2018

(54) ULTRASOUND DIAGNOSTIC APPARATUS MANAGEMENT SYSTEM

(71) Applicants: SAMSUNG MEDISON CO., LTD., Gangwon-Do (KR); SAMSUNG ELECTRONICS CO., LTD., Suwon-si, Gyeonggi-do (KR)

(72) Inventors: Sung Do Kwon, Yongin-si (KR); Jong Mock Lee, Yongin-si (KR)

(73) Assignees: SAMSUNG MEDISON CO., LTD., Hongcheon-gun, Gangwon-do (KR); SAMSUNG ELECTRONICS CO., LTD., Sunwon-si, Gyeonggi-do (KR)

( * ) Notice: Subject to any disclaimer, the term of this patent is extended or adjusted under 35 U.S.C. 154(b) by 527 days.

(21) Appl. No.: 14/560,725

(22) Filed: Dec. 4, 2014

(65) Prior Publication Data

US 2015/0182193 A1   Jul. 2, 2015

(30) Foreign Application Priority Data

Dec. 27, 2013 (KR) ........................ 10-2013-0164903

(51) Int. Cl.
  *A61B 8/00* (2006.01)
  *H01L 41/257* (2013.01)
  (Continued)

(52) U.S. Cl.
  CPC .............. *A61B 8/4433* (2013.01); *A61B 8/56* (2013.01); *A61B 8/58* (2013.01); *G01N 29/0672* (2013.01);
  (Continued)

(58) Field of Classification Search
  CPC ........... A61B 8/4433; A61B 8/56; A61B 8/58; G01S 7/5205; G01S 7/52079; H01L 41/257
  See application file for complete search history.

(56) References Cited

U.S. PATENT DOCUMENTS 6,464,925 B1 * 10/2002 Tomohiro ............. H01L 41/257
                                                  264/40.1
6,497,660 B1   12/2002 Dillman et al.
(Continued)

FOREIGN PATENT DOCUMENTS

JP    2011-211059 A    10/2011

OTHER PUBLICATIONS

Extended European Search Report issued in European Application No. 14187029.5, dated Mar. 18, 2015.

*Primary Examiner* — Long V Le
*Assistant Examiner* — Angela M Hoffa
(74) *Attorney, Agent, or Firm* — McDermott Will & Emery LLP

(57) ABSTRACT

There are provided an ultrasound diagnostic apparatus management system and a method of controlling the ultrasound diagnostic apparatus management system. The ultrasound diagnostic apparatus management system may include a diagnosis unit including an acoustic module and a connecting unit of the diagnosis unit; a rearrangement unit including a connecting unit for rearrangement in which the connecting unit of the diagnosis unit is docked and a power supply unit for rearrangement; a detecting unit configured to measure a capacitance of the acoustic module; and a control unit configured to control such that the power supply unit for rearrangement applies a voltage for rearrangement to the acoustic module when the measured capacitance is a predetermined value or less.

14 Claims, 11 Drawing Sheets

(51) Int. Cl.
*G01N 29/06* (2006.01)
*G01S 7/52* (2006.01)
*G01S 15/89* (2006.01)

(52) U.S. Cl.
CPC ........ *G01S 7/5205* (2013.01); *G01S 7/52079* (2013.01); *G01S 15/8915* (2013.01); *H01L 41/257* (2013.01); *A61B 8/4405* (2013.01); *A61B 8/4472* (2013.01); *A61B 8/54* (2013.01)

(56) References Cited

U.S. PATENT DOCUMENTS

| | | |
|---|---|---|
| 9,112,142 B2 * | 8/2015 | Nakazawa ............ G01B 17/00 |
| 2004/0150963 A1 | 8/2004 | Holmberg et al. |
| 2004/0179332 A1 | 9/2004 | Smith et al. |
| 2004/0260181 A1 * | 12/2004 | Makita .................. H01L 41/257 |
| | | 600/459 |
| 2009/0299192 A1 | 12/2009 | Asafusa et al. |
| 2012/0265027 A1 | 10/2012 | Lee et al. |
| 2012/0319529 A1 | 12/2012 | Nakazawa et al. |
| 2012/0323514 A1 * | 12/2012 | Nakazawa ............ G01B 17/00 |
| | | 702/65 |

\* cited by examiner

ULTRASOUND DIAGNOSTIC APPARATUS MANAGEMENT SYSTEM

CROSS-REFERENCE TO RELATED APPLICATION

This application claims the benefit of Korean Patent Application No. P2013-0164903, filed on Dec. 27, 2013 in the Korean Intellectual Property Office, the disclosure of which is incorporated herein by reference.

BACKGROUND

1. Field

Embodiments of the present invention relate to an ultrasound diagnostic apparatus management system that can improve performance of an ultrasound diagnostic apparatus having degraded performance due to a long-term usage or other reasons and promote hygiene of a subject by maintaining a clean ultrasound diagnostic apparatus, and a method of controlling the ultrasound diagnostic apparatus management system.

2. Description of the Related Art

An ultrasound diagnostic apparatus is an apparatus that radiates an ultrasound signal toward a desired region inside a body from a body surface of a subject and obtains a tomogram of a soft tissue or an image of a blood flow in a non-invasive manner using information on a reflected ultrasound signal (ultrasound echo signal). The ultrasound diagnostic apparatus is advantageous in that it is small, cheap, can display in real time, and has high safety due to no exposure to X-rays, compared to other image diagnostic apparatuses such as an X-ray diagnostic apparatus, an X-ray computerized tomography (CT) scanner, a magnetic resonance imaging (MRI) apparatus, and a nuclear medicine diagnostic apparatus. Due to these advantages, the ultrasound diagnostic apparatus is being widely used for heart, abdomen, urinary organ, and obstetrics diagnoses.

The ultrasound diagnostic apparatus transmits an ultrasound signal to the subject in order to obtain an ultrasound image of the subject, and includes an ultrasound diagnostic apparatus for receiving an ultrasound echo signal reflected from the subject.

The ultrasound diagnostic apparatus includes a transducer. Here, the transducer may include a piezoelectric layer configured to mutually convert an electrical signal and an acoustic signal by vibrating a piezoelectric material, a matching layer configured to reduce an acoustic impedance difference between the piezoelectric layer and the subject such that an ultrasound generated from the piezoelectric layer is delivered to the subject maximally, a lens layer configured to focus the ultrasound propagating to a front of the piezoelectric layer to a specific point, and an absorbing layer configured to prevent image distortion by blocking the ultrasound from propagating to a rear of the piezoelectric layer.

Due to a long-term usage or other reasons, in the piezoelectric layer of the ultrasound diagnostic apparatus, a polarization array of the piezoelectric layer is shifted. As a result, piezoelectric performance may be degraded. A great deal of research on such problems has been conducted.

SUMMARY

The present invention provides an ultrasound diagnostic apparatus management system in which, after an ultrasound diagnostic apparatus is docked in a rearrangement unit, a capacitance of an acoustic module is measured, and a voltage for rearrangement is applied to the acoustic module until a value thereof exceeds a predetermined value, and a method of controlling the ultrasound diagnostic apparatus management system.

According to an aspect of the present invention, there is provided an ultrasound diagnostic apparatus management system. The system may include a diagnosis unit including an acoustic module and a connecting unit of the diagnosis unit; a rearrangement unit including a connecting unit for rearrangement in which the connecting unit of the diagnosis unit is docked and a power supply unit for rearrangement; a detecting unit configured to measure a capacitance of the acoustic module; and a control unit configured to control such that the power supply unit for rearrangement applies a voltage for rearrangement to the acoustic module when the measured capacitance is a predetermined value or less.

Also, according to the embodiment, by switching between an ultrasound-generation-signal receiving unit and the connecting unit of the diagnosis unit, it is possible to prevent a reverse voltage from entering the ultrasound-generation-signal receiving unit.

Also, according to the embodiment, an ultrasound generation signal may be wirelessly received, and the power supply unit for rearrangement may wirelessly apply the voltage for rearrangement.

Also, according to the embodiment, the system may include a cleaning unit configured to clean an ultrasound diagnostic apparatus and a sterilizing unit configured to sterilize the ultrasound diagnostic apparatus.

According to another aspect of the present invention, there is provided a method of controlling an ultrasound diagnostic apparatus management system. The method may include docking a diagnosis unit in a power supply unit for rearrangement; measuring a capacitance of an acoustic module in the diagnosis unit; and applying, by the power supply unit for rearrangement, a voltage for rearrangement to the acoustic module of the docked diagnosis unit when the measured capacitance is a predetermined value or less.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
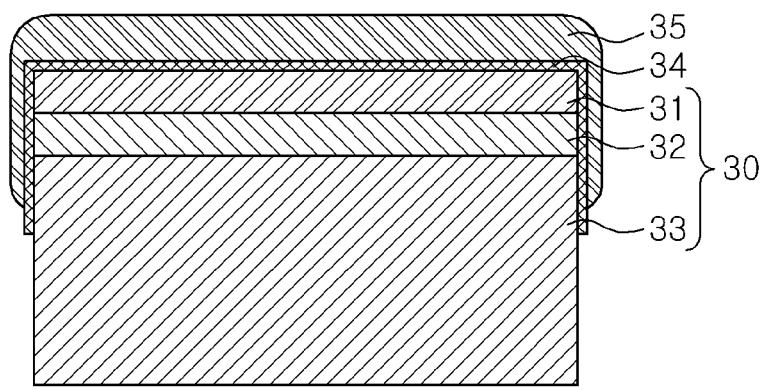
FIG. 1 is a cross-sectional view of an acoustic module in a diagnosis unit according to an embodiment.

Hereinafter, in order to facilitate understanding and reproduce by those skilled in the art, the present invention will be described in detail by explaining exemplary embodiments with reference to the accompanying drawings. When it is determined that detailed explanations of related well-known functions or configurations unnecessarily obscure the gist of the embodiments, the detailed description thereof will be omitted.

Terms described in below are selected by considering functions in the embodiment and meanings may vary depending on, for example, a user or operator's intentions or customs. Therefore, in the following embodiments, when terms are specifically defined, the meanings of terms should be interpreted based on definitions, and otherwise, should be interpreted based on general meanings recognized by those skilled in the art.

Also, although configurations of selectively described aspects or selectively described embodiments in below are illustrated as a single integrated configuration in the drawings, unless otherwise described, it should be understood that these are freely combined with each other when technological contradiction of these combinations is not apparent for those skilled in the art.

Hereinafter, an embodiment of an ultrasound diagnostic apparatus management system will be described with the accompanying drawings.

FIG. 1 illustrates a cross-section of an acoustic module provided in an ultrasound diagnosis unit according to an embodiment.

As illustrated in FIG. 1, an ultrasound diagnosis unit 2 may include an acoustic module 30 having a piezoelectric layer 32, an absorbing layer 33 provided below the piezoelectric layer 32, and a matching layer 31 provided above the piezoelectric layer 32, a protection layer 34 configured to cover an upper surface and a part of a side surface of the acoustic module 30, and a lens layer 35 configured to cover an upper surface and a side surface of the protection layer 34.

The acoustic module 30 may also be called an ultrasound transducer. As the ultrasound transducer, a magnetostrictive ultrasonic transducer using a magnetostrictive effect of a magnetic material, a capacitive micromachined ultrasonic transducer that transmits and receives an ultrasound using vibration of several hundreds or thousands of micromachined thin films, and a piezoelectric ultrasonic transducer using a piezoelectric effect of a piezoelectric material may be used. Hereinafter, the piezoelectric ultrasonic transducer will be described as an example of the transducer.

A voltage is generated when a mechanical pressure is applied to a predetermined material and mechanical deformation occurs when the voltage is applied, which is called a piezoelectric effect and a converse piezoelectric effect. A material having these effects may be called a piezoelectric material. That is, the piezoelectric material may be a material that converts electrical energy into mechanical vibration energy and mechanical vibration energy into electrical energy.

The ultrasound diagnosis unit 2 may include the piezoelectric layer 32 made of a piezoelectric material that generates an ultrasound by converting an electrical signal into mechanical vibration when the electrical signal is applied.

The piezoelectric material forming the piezoelectric layer 32 may include a ceramic of lead zirconate titanate (PZT), PMN-PT single crystals made of a solid solution of lead magnesium niobate and lead titanate, or PZNT single crystals made of a solid solution of lead zinc niobate and lead titanate. Alternatively, various materials for converting an electrical signal into mechanical vibration may also be used as an example of the piezoelectric material forming the piezoelectric layer 32.

Also, the piezoelectric layer 32 may also be arranged in a single layer structure or a multilayer stacked structure. In general, when the piezoelectric layer 32 having a stacked structure is used, it is easy to adjust an impedance and a voltage, thereby obtaining good sensitivity and energy conversion efficiency, and a smooth spectrum. Alternatively, for performance of the piezoelectric layer 32, various structures may also be used as an example of the structure of the piezoelectric layer 32.

The absorbing layer 33 is provided below the piezoelectric layer 32, absorbs the ultrasound that is generated from the piezoelectric layer 32 and propagates to a rear thereof. Therefore, it is possible to prevent the ultrasound from propagating to a rear of the piezoelectric layer 32. Thus, the absorbing layer 33 prevents an image from being distorted. In order to improve an attenuation or blocking effect of the ultrasound, the absorbing layer 33 may be manufactured in a plurality of layers. Alternatively, in order to improve the attenuation or blocking effect of the ultrasound, various structures may also be used as an example of the structure of the absorbing layer 33.

The matching layer 31 may be provided above the piezoelectric layer 32. The matching layer 31 reduces an acoustic impedance difference between the piezoelectric layer 32 and a subject and matches acoustic impedances of the piezoelectric layer 32 and the subject, which causes the ultrasound generated from the piezoelectric layer 32 to be efficiently delivered to the subject. For this purpose, the matching layer 31 may have an intermediate value between the acoustic impedance of the piezoelectric layer 32 and the acoustic impedance of the subject.

The matching layer 31 may be made of a glass or resin material. Alternatively, in order to match the acoustic impedances of the piezoelectric layer 32 and the subject, various materials may also be used as an example of the material forming the matching layer 31.

In addition, the matching layer 31 may be constituted by a plurality of matching layers 31 such that the acoustic impedance gradually changes from the piezoelectric layer 32 to the subject, and the plurality of matching layers 31 may be made of different materials. Alternatively, in order to gradually change the acoustic impedance, various structures may also be used as an example of the structure of the matching layer 31.

Also, the piezoelectric layer 32 and the matching layer 31 may be processed in a 2D array form having a matrix form or in a 1D array form by a dicing process.

The protection layer 34 may be provided to cover an upper surface of the matching layer 31 and a part of a side surface of the acoustic module 30. The protection layer 34 may include a chemical shield that can protect internal components from water and chemicals used for disinfection and the like by coating or depositing a conductive material onto a surface of a moisture-resistant and chemical-resistant film. The chemical shield may be formed such that a polymer film is formed in the upper surface of the matching layer 31 and a part of the side surface of the acoustic module 30 by performing parylene coating. Also, the chemical shield may be formed by applying cross-section sputtering to the polymer film.

Also, the protection layer 34 may include a radio frequency shield (RF Shield) that can prevent a high-frequency component, which can be generated from the piezoelectric layer 32, from being leaked to the outside and block entering of an external high-frequency signal. Alternatively, in order to block inflows and outflows of the high-frequency component, various configurations may also be used as an example of the configuration of the protection layer 34.

The lens layer 35 may be provided to cover an upper surface and a side surface of the protection layer 34. The lens layer 35 may use a low-attenuation material in order to prevent an ultrasound signal generated from the piezoelectric layer 32 from being attenuated. For example, an epoxy such as a low viscosity epoxy resin (DER322) or DEH24 may be used. Alternatively, in order to prevent attenuation of the ultrasound signal, various materials may also be used as an example of the material of the lens layer 35. In this manner, when the lens layer 35 is made of the low-attenuation material, it is possible to improve sensitivity of the ultrasound signal.

Also, the lens layer 35 is provided to cover a part of a kerf of the acoustic module 30, which is a part of a side surface of the acoustic module 30, thereby reducing crosstalk.

Hereinafter, a molecular structure of Perovskite 4 forming the piezoelectric layer 32 according to the embodiment will be examined and rearrangement of the piezoelectric layer 32 will be described with reference to FIG. 2.

Figure 2:
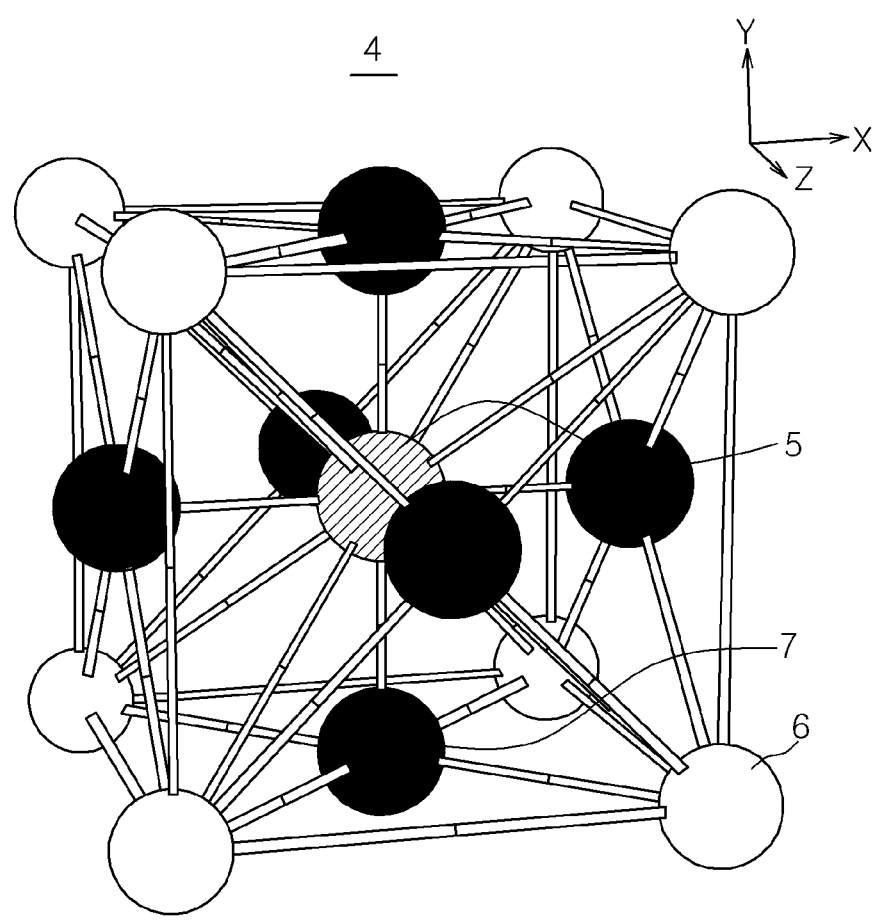
FIG. 2 is a perspective view of a Perovskite crystal structure of a piezoelectric layer molecule of the acoustic module according to the embodiment.

FIG. 2 illustrates a molecular structure of Perovskite 4 of the piezoelectric layer 32 of the acoustic module according to the embodiment.

Perovskite is one of crystal structures and may be a crystal structure of most of double oxides represented as a chemical formula $RMX_3$. In general, a ceramic used as the piezoelectric material may have a crystal structure Perovskite 4.

As illustrated in FIG. 2, in the crystal structure of Perovskite 4, a white circle 6 may indicate an atom R, a circle 5 having an oblique line therein may indicate an atom M, and a black circle 7 may indicate an atom X. Atoms R indicated by the white circle 6 form a simple cubic lattice, the atom M indicated by the circle 5 having an oblique line therein is in a center thereof, and the atom X indicated by the black circle 7 may be in a center of a plane including the atoms R indicated by four white circles 6.

In the crystal structure of Perovskite 4, the atom M indicated by the circle 5 having an oblique line therein may be positioned apart from the center in an ionic state. Accordingly, when the piezoelectric layer 32 is manufactured, in order to generate mechanical vibration in a constant direction, a poling voltage, which is a strong DC electric field, is applied such that molecules having the crystal structure of Perovskite 4 may be arranged to have constant directivity.

The piezoelectric layer 32 in which the poling voltage is applied and internal molecules of the piezoelectric layer 32 having the crystal structure of Perovskite 4 such as a ceramic are arranged in a one direction may fail to keep the constant directivity due to a long-term usage or other reasons. Accordingly, a capacitance of the piezoelectric layer 32 having the crystal structure of Perovskite 4 may decrease. In this case, a power supply unit for rearrangement 40 of a rearrangement unit applies a voltage to the piezoelectric layer 32 of the diagnosis unit 2 such that the constant directivity is restored. In this way, a reduced piezoelectric capability of the acoustic module 30 in the ultrasound diagnosis unit 2 may be improved.

Hereinafter, an ultrasound diagnostic apparatus management system 1 including a diagnosis unit 2 and a rearrangement unit 3 according to an embodiment will be described with reference to FIGS. 3 to 6.

Figure 3:
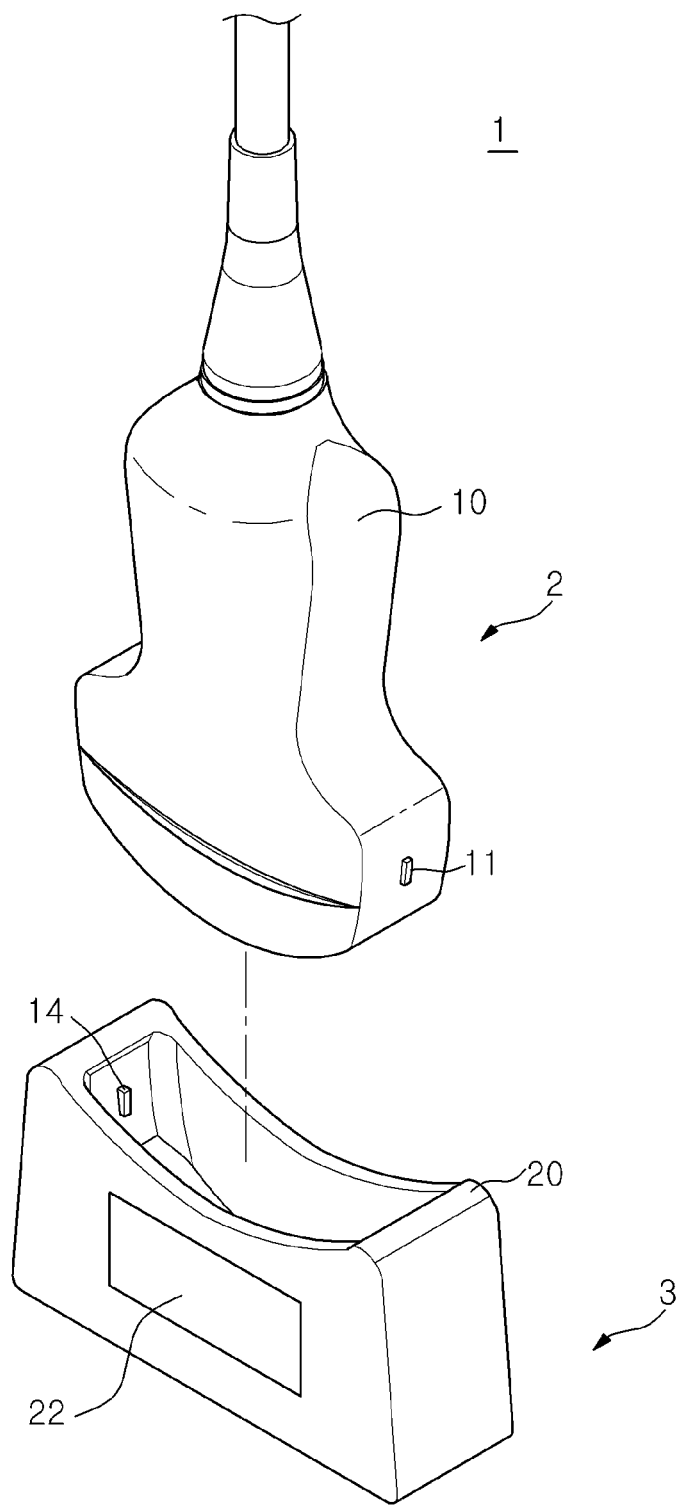
FIG. 3 is a perspective view of an appearance an ultrasound diagnostic apparatus management system before the diagnosis unit is docked in a rearrangement unit according to the embodiment.
Figure 4:
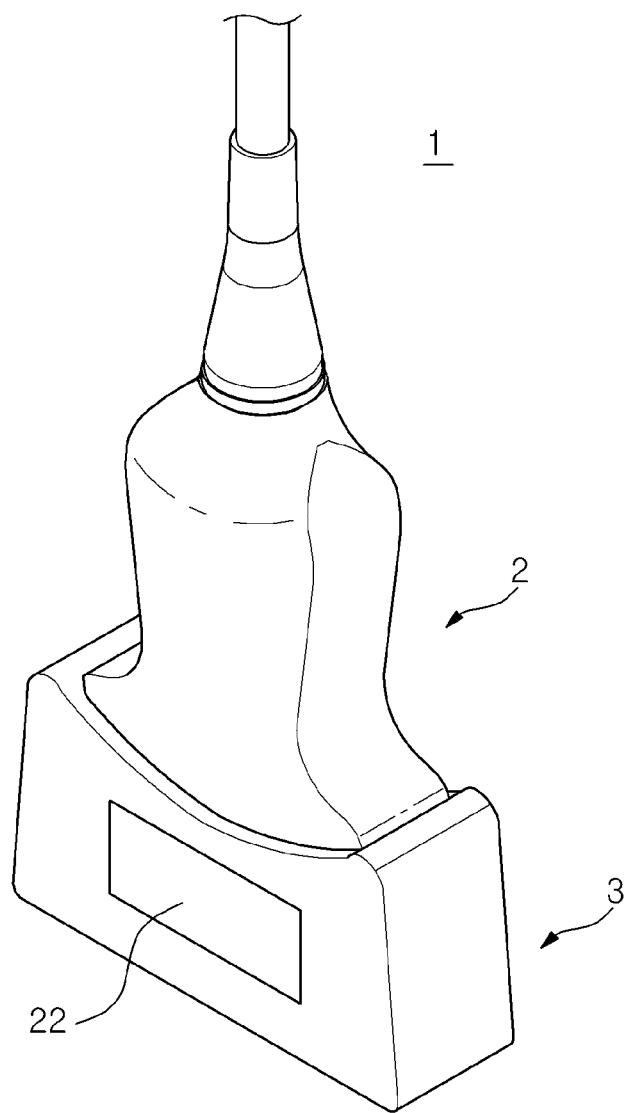
FIG. 4 is a perspective view of an appearance of the ultrasound diagnostic apparatus management system after the diagnosis unit is docked in the rearrangement unit according to the embodiment.
Figure 5:
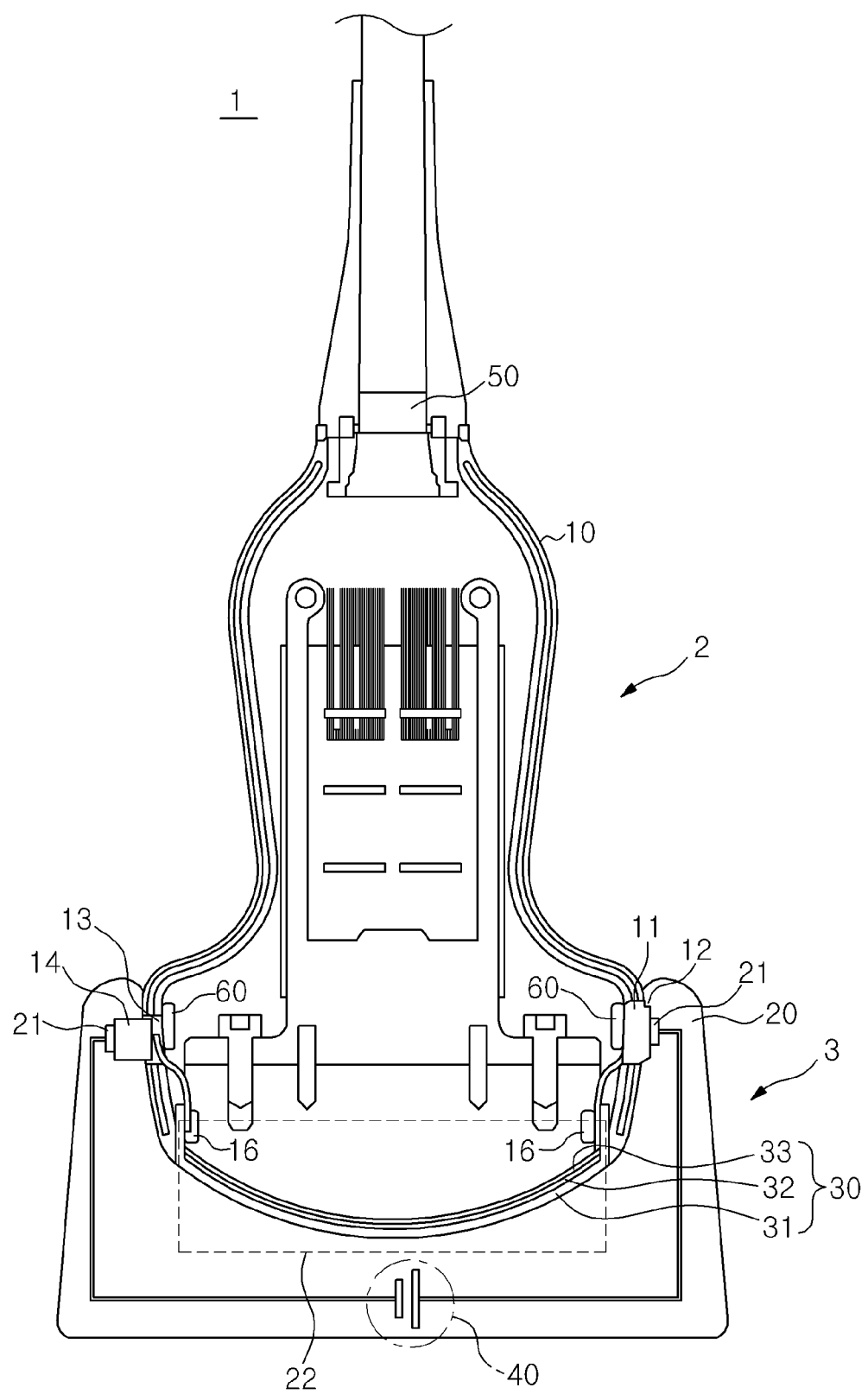
FIG. 5 is a cross-sectional view of the ultrasound diagnostic apparatus management system after the diagnosis unit is docked in the rearrangement unit according to the embodiment.

FIG. 3 illustrates an appearance of the ultrasound diagnostic apparatus management system 1 before the diagnosis unit 2 is docked in the rearrangement unit 3 according to the embodiment. FIG. 4 illustrates an appearance of the ultrasound diagnostic apparatus management system 1 after the diagnosis unit 2 is docked in the rearrangement unit 3 according to the embodiment. Also, FIG. 5 illustrates a cross-section of the ultrasound diagnostic apparatus management system 1 after the diagnosis unit 2 is docked in the rearrangement unit 3 according to the embodiment.

The ultrasound diagnostic apparatus management system 1 may include the diagnosis unit 2 and the rearrangement unit 3.

The diagnosis unit 2 may include a diagnosis unit housing 10, the acoustic module 30, a detecting unit 16, an ultrasound-generation-signal receiving unit 50, a switching unit 60, a first connecting unit 11 of the diagnosis unit, and a second connecting unit 13 of the diagnosis unit.

The diagnosis unit housing 10 may include various components necessary for driving the diagnosis unit 2. Specifically, the diagnosis unit housing 10 may protect various embedded components in safety and provide a function of stably fixing the various components. The diagnosis unit housing 10 may include a central processing unit (CPU) serving as a control unit, various processing units such as a graphic processing unit (GPU), a printed circuit board (PCB), and the like therein, and may also include various types of storage devices therein as necessary.

The CPU installed in the diagnosis unit housing 10 may serve as a control unit and may be a kind of a microprocessor. The microprocessor is a processing device in which an arithmetic logic calculator, a register, a program counter, a command decoder, a control circuit, and the like are integrated into at least one silicon chip. The CPU generates a control signal for controlling operations of the diagnosis unit 2 or the rearrangement unit 3, and may deliver the generated control signal to the acoustic module 30, the detecting unit 16, the ultrasound-generation-signal receiving unit 50, the switching unit 60, and the power supply unit for rearrangement. Depending on embodiments, the CPU determines whether the capacitance of the acoustic module 30 measured by the detecting unit 16 is a predetermined value or less, may instruct that the acoustic module 30 and a connecting unit for rearrangement are electrically connected through switching of the switching unit 60 and that a voltage for rearrangement is applied to the acoustic module 30, and may also preform signal processing of a received ultrasound.

The GPU refers to a processing unit for processing information on graphics usually out of microprocessors. The GPU may assist a graphic processing function of the CPU or independently perform graphic processing. Depending on embodiments, the GPU may perform signal processing for converting the ultrasound signal received by the acoustic module 30 into an ultrasound image signal or signal processing for displaying a currently measured capacitance of the acoustic module 30 and operations of the ultrasound diagnostic apparatus management system.

The PCB is a board in which a predetermined circuit is printed. The CPU, the GPU, and various storage devices may be installed in the PCB. Depending on embodiments, the PCB may be fixed in an inner side surface of the diagnosis unit housing 10 and provide a function of stably fixing the CPU and the like.

The diagnosis unit housing 10 may include various storage devices therein. The storage device may include a magnetic disk storage device that stores data by magnetizing a magnetic disk surface and a semiconductor memory device that stores data using various types of memory semiconductors. In consideration of a material, a size, a thickness, and other variables of the acoustic module 30, the storage device may store a predetermined capacitance of the acoustic module 30 in order for the acoustic module 30 to have predetermined piezoelectric performance or more, a currently measured capacitance of the acoustic module 30, the voltage for rearrangement to be applied by the power supply unit for rearrangement, and the like.

Also, the diagnosis unit housing 10 may further include a power source for supplying power to various components inside the housing or the rearrangement unit 3.

The acoustic module 30 is positioned in a front surface of the diagnosis unit 2, and may include the matching layer 31, the piezoelectric layer 32, and the absorbing layer 33. As described above, the matching layer 31 reduces an acoustic impedance difference between the piezoelectric layer 32 and the subject, and matches acoustic impedances of the piezoelectric layer 32 and the subject, which causes the ultrasound generated from the piezoelectric layer 32 to be efficiently delivered to the subject. When an electrical signal is applied, the piezoelectric layer 32 converts the electrical signal into mechanical vibration, the absorbing layer 33 absorbs the ultrasound that is generated from the piezoelectric layer and propagates backward so that it is possible to block the ultrasound from propagating to a rear of the piezoelectric layer 32.

Materials and structural shapes of the matching layer 31, the piezoelectric layer 32, and the absorbing layer 33 may be the same as those in the above description.

The detecting unit 16 measures a capacitance of the piezoelectric layer 32 of the acoustic module 30 and may be positioned at both sides of the acoustic module 30.

Measurement of the capacitance may be performed such that an AC voltage is applied to measure a current flowing in the piezoelectric layer 32 and the measured current is converted into a capacitance. The detecting unit 16 may use a digital multi meter (DMM) or an analog multi meter (AMM). Alternatively, in order to measure the capacitance of the piezoelectric layer 32, the detecting unit 16 of various methods may also be used as an example.

The ultrasound-generation-signal receiving unit 50 is positioned in a rear surface of the diagnosis unit 2, may receive a signal for controlling the diagnosis unit 2 from the outside, and may also receive a signal for controlling the rearrangement unit 3 depending on the embodiment.

Also, the ultrasound-generation-signal receiving unit 50 may receive a control signal from the outside via wired and/or wireless communication. Specifically, the ultrasound-generation-signal receiving unit 50 may include an infrared (IR) communication module, an RF receiving antenna, and the like. Alternatively, various elements for wireless communication may also be used as an example of the ultrasound-generation-signal receiving unit.

The switching unit 60 is provided adjacent to the connecting unit of the diagnosis unit. When there is no input signal for rearrangement, the switching unit 60 electrically connects the acoustic module 30 and the ultrasound-generation-signal receiving unit 50. However, when the input signal for rearrangement is received, the switching unit 60 may electrically connect the acoustic module 30 and the power supply unit for rearrangement through switching.

Also, since the switching unit 60 needs to correspond to the voltage for rearrangement causing a strong electric field, a photocoupler for a high voltage, a transistor, or an FET may be used. Alternatively, a configuration in which the voltage for rearrangement does not enter the ultrasound-generation-signal receiving unit 50 may also be used as an example of the switching unit 60.

The first connecting unit 11 of the diagnosis unit and the second connecting unit 13 of the diagnosis unit are positioned at both sides of the diagnosis unit and may be electrically connected to a first connecting unit for rearrangement 12 and a second connecting unit for rearrangement 14, respectively.

Similar to the above-described switching unit 60, since a high voltage for rearrangement of the rearrangement unit 3 is applied, a material that has excellent conductivity at a high voltage and prevents the voltage from being leaked to the outside may be used as an example of the connecting unit of the diagnosis unit.

Also, the diagnosis unit includes a plurality of connecting units. In order for a user to easily identify directivity of the diagnosis unit 2 docked in the rearrangement unit 3, the plurality of connecting units of the diagnosis unit may have different shapes. These different shapes will be described below.

The rearrangement unit 3 may include a rearrangement unit housing 20, the power supply unit for rearrangement 40, a detecting unit 21, a display unit 22, the first connecting unit for rearrangement 12, and the second connecting unit for rearrangement 14.

Similar to the diagnosis unit housing 10, the rearrangement unit housing 20 may include various components necessary for driving the diagnosis unit 2. Specifically, the rearrangement unit housing 20 may protect the various embedded components in safety and provide a function of stably fixing the various components. The rearrangement unit housing 20 may include a central processing unit (CPU) serving as a control unit, various processing units such as a graphic processing unit (GPU), a printed circuit board (PCB), and the like therein, and may also include various types of storage devices therein as necessary. Also, the CPU included in the the rearrangement unit housing 20 may serve as a control unit.

Kinds and functions of the various components included in the rearrangement unit housing 20 may be the same as those in the above-described diagnosis unit housing 10 or may differ.

The power supply unit for rearrangement 40 is included in the rearrangement unit housing 20, is electrically connected to the diagnosis unit 2, and may provide the voltage for rearrangement to the piezoelectric layer 32 when an input signal for rearrangement is applied. In general, the voltage for rearrangement may be provided by power provided from the outside and the voltage for rearrangement may also be wirelessly provided without power provided from the outside via a wired line.

Specifically, the voltage for rearrangement may be provided using a battery and a voltage amplifying circuit, and the voltage for rearrangement may also be provided by charging a battery wirelessly. Alternatively, various methods of providing the voltage for rearrangement without power provided from the outside via a wired line may also be used as an example of a wireless power supply device.

Also, the voltage for rearrangement provided from the power supply unit for rearrangement 40 needs a strong electric field in order to constantly change directivity of the crystal structure of Perovskite 4 of the piezoelectric layer 32, and thereby a high voltage is necessary. Specifically, in consideration of various components of the ultrasound diagnostic apparatus management system, a predetermined voltage for rearrangement in a range of 100 [V] to 200 [V] may be provided. Alternatively, the voltage for rearrangement determined by the user's input may be provided.

The detecting unit 21 may measure a capacitance of the piezoelectric layer in the acoustic module of the diagnosis unit 2. Functions, shapes, materials, and the like of the detecting unit 21 included in the rearrangement unit may be the same as those in the detecting unit 16 included in the above-described diagnosis unit 2 or may differ.

The display unit 22 may display operations of the ultrasound diagnostic apparatus management system. Specifically, the display unit 22 may display the capacitance of the piezoelectric layer measured by the detecting unit 16 of the diagnosis unit or the detecting unit 21 of the rearrangement unit, errors of the piezoelectric layer based on the measured capacitance, a rearrangement operation, completion of the rearrangement operation, a cleaning operation, a sterilization operation, and the like.

The first connecting unit for rearrangement 12 and the second connecting unit for rearrangement 14 are positioned at both sides of the diagnosis unit 2 and may be electrically connected to the first connecting unit 11 of the diagnosis unit and the second connecting unit 13 of the diagnosis unit, respectively.

Since a high voltage for rearrangement of the rearrangement unit 3 is applied, a material that has excellent conductivity at a high voltage and prevents the voltage from being leaked to the outside may be used as an example of the connecting unit for rearrangement.

Also, a plurality of connecting units for rearrangement are provided. In order for the user to easily identify directivity of the diagnosis unit 2 docked in the rearrangement unit 3, the plurality of connecting units for rearrangement may have different shapes. These different shapes will be described below.

Depending on the embodiment, the rearrangement unit 3 may also include a cleaning unit and a sterilizing unit.

The cleaning unit may remove a foreign material existing on a surface of the diagnosis unit 2. Specifically, a brush in the form of a hairbrush is provided in an inner side of the rearrangement unit 3 and eliminates the foreign material existing on the surface of the diagnosis unit 2. A cleaning solution is injected into an inner side of a rearrangement housing and eliminates the foreign material existing on the surface of the diagnosis unit 2 using the brush or ultrasound vibration. Alternatively, in order to eliminate the foreign material existing on the surface of the diagnosis unit 2, various methods, structures, and the like may also be used as an example of the cleaning unit.

The sterilizing unit eliminates bacteria in the diagnosis unit 2, thereby improving hygiene of the subject. Specifically, an ultraviolet light generator is provided in the inner side of the rearrangement unit 3, and the bacteria in the diagnosis unit 2 may be eliminated through ultraviolet light provided by the ultraviolet light generator. Similar to the cleaning solution, a sterilizing solution is injected into the inner side of the rearrangement housing, and the bacteria may be eliminated using vibration of the ultrasound. Also, the rearrangement housing is made of a material including silver ions (AG+), and thereby a sterilization effect may be obtained. Alternatively, in order to eliminate the bacteria in the diagnosis unit 2, various methods, structures, and the like may also be used as an example of the sterilizing unit.

Hereinafter, a shape of the connecting unit which allows the user to easily recognize directivity of the diagnosis unit docked in the rearrangement unit 3 using the connecting units for rearrangement having different shapes according to the embodiment will be described with reference to FIGS. 6A and 6B.

Figure 6A:
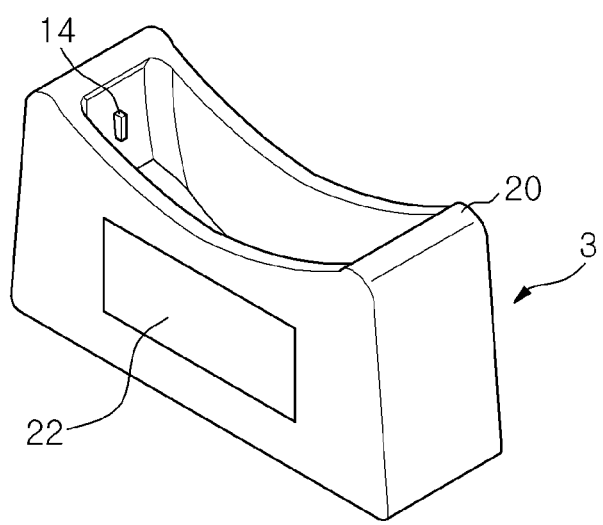
FIGS. 6A and 6B are perspective views of the rearrangement unit including two connecting units for rearrangement having asymmetric shapes according to the embodiment.
Figure 6B:
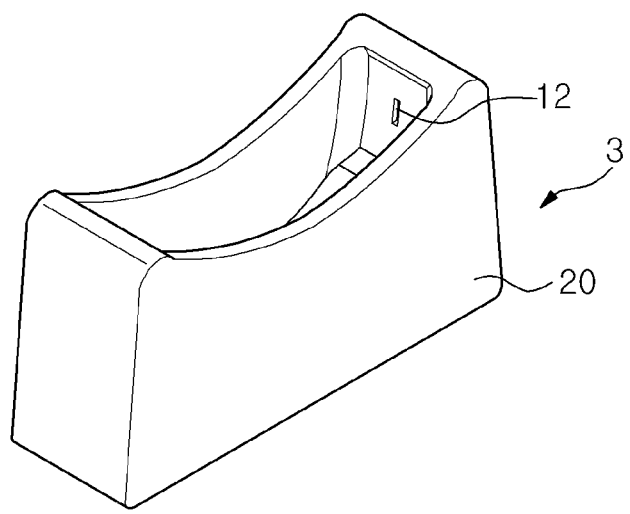

FIGS. 6A and 6B illustrate the rearrangement unit 3 including two connecting units for rearrangement having asymmetric shapes according to the embodiment.

The connecting unit for rearrangement may provide the voltage for rearrangement provided from the power supply unit for rearrangement 40 of the rearrangement unit 3 to the piezoelectric layer 32 of the acoustic module 30 through the connecting unit of the diagnosis unit. As illustrated in FIGS. 6A and 6B, the connecting unit for rearrangement may be positioned at two positions of an inner side surface of the rearrangement housing.

Also, the first connecting unit for rearrangement 12 and the first connecting unit 11 of the diagnosis unit, and the second connecting unit for rearrangement 14 and the second connecting unit 13 of the diagnosis unit are structurally connected in corresponding male and female pairs. However, the first connecting unit for rearrangement 12 and the second connecting unit 13 of the diagnosis unit, and the second connecting unit for rearrangement 14 and the first connecting unit 11 of the diagnosis unit have non-corresponding male and female pairs. As a result, the first connecting unit for rearrangement 12 and the second connecting unit 13 of the diagnosis unit, and the second connecting unit for rearrangement 14 and the first connecting unit 11 of the diagnosis unit may not be structurally and electrically connected.

For example, as illustrated in FIGS. 6A and 6B, the first connecting unit for rearrangement 12 may have a groove formed therein. The second connecting unit for rearrangement 14 may be formed in a shape projecting outward. Also, the first connecting unit of the connecting unit may be formed in a shape projecting outward, and the second connecting unit of the connecting unit may have a groove formed inward. In this manner, structural or electrical connections may be provided between the first connecting unit for rearrangement 12 and the first connecting unit 11 of the diagnosis unit, and between the second connecting unit for rearrangement 14 and the second connecting unit 13 of the diagnosis unit. However, structural or electrical connections may not be provided between the first connecting unit for rearrangement 12 and the second connecting unit 13 of the diagnosis unit, and between the second connecting unit for rearrangement 14 and the first connecting unit 11 of the diagnosis unit.

According to this structure, when the user inserts the diagnosis unit to be docked in the rearrangement unit 3 in a direction in which the first connecting unit for rearrangement 12 matches with the first connecting unit 11 of the diagnosis unit and the second connecting unit for rearrangement 14 matches with the second connecting unit 13 of the diagnosis unit, easy docking is possible. However, when the user inserts the diagnosis unit to be docked in the rearrangement unit 3 in a direction in which the first connecting unit for rearrangement 12 matches with the second connecting unit 13 of the diagnosis unit and the second connecting unit for rearrangement 14 matches with the first connecting unit 11 of the diagnosis unit, docking is not possible. In this manner, the user may easily identify directivity of the diagnosis unit docked in the rearrangement unit 3.

Alternatively, various shapes and numbers of the connecting units in which the user can easily identify directivity between the rearrangement unit 3 and the diagnosis unit may also be used as examples of the connecting unit for rearrangement and the connecting unit of the diagnosis unit.

Hereinafter, the switching unit 60 for removing impacts applied on various components of the ultrasound diagnostic apparatus management system due to a surge voltage or a reverse voltage according to the embodiment will be described with reference to FIGS. 7A and 7B.

Figure 7A:
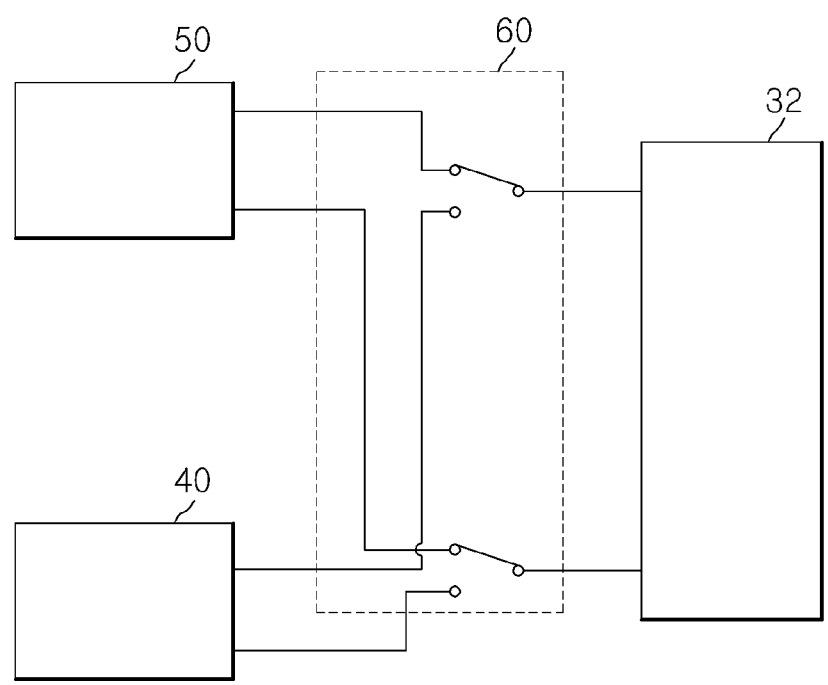
FIGS. 7A and 7B are conceptual diagrams illustrating a switching unit that is connected to a piezoelectric layer by switching between an ultrasound-generation-signal receiving unit and the connecting unit of the diagnosis unit according to the embodiment.
Figure 7B:
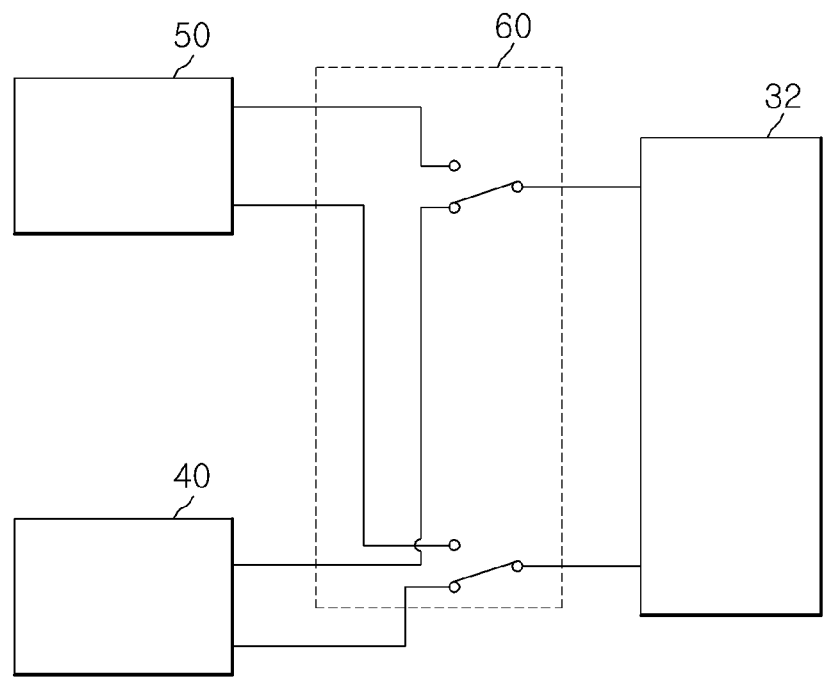

FIG. 7A illustrates a case in which the switching unit 60 connects between the ultrasound-generation-signal receiving unit 50 and the piezoelectric layer 32 of the acoustic module. FIG. 7B illustrates a case in which the switching unit 60 connects between the power supply unit for rearrangement 40 and the piezoelectric layer 32 of the acoustic module.

Since the voltage for rearrangement provided from the power supply unit for rearrangement 40 to the piezoelectric layer 32 of the acoustic module is high, the voltage for rearrangement may be delivered to not only the piezoelectric layer 32 of the acoustic module but also various components of the diagnosis unit including the ultrasound-generation-signal receiving unit, thereby causing impacts. In order to prevent such impacts, the entering voltage for rearrangement may be controlled by the switching unit 60.

When the diagnosis unit does not perform a rearrangement operation, as illustrated in FIG. 7A, the switching unit 60 connects between the ultrasound-generation-signal receiving unit 50 and the piezoelectric layer 32 of the acoustic module, and an ultrasound image may be obtained by transmitting and receiving an ultrasound. However, when the diagnosis unit performs a rearrangement operation, as illustrated in FIG. 7B, the switching unit 60 connects between the power supply unit for rearrangement 40 and the piezoelectric layer 32 of the acoustic module, disables an electrical connection with the ultrasound-generation-signal receiving unit 50, and thereby the voltage for rearrangement does not enter the ultrasound-generation-signal receiving unit 50.

Also, since the switching unit 60 needs to correspond to the voltage for rearrangement causing a strong electric field, a photocoupler for a high voltage, a transistor, or an FET may be used. Alternatively, a configuration in which the voltage for rearrangement does not enter the ultrasound-generation-signal receiving unit 50 may also be used as an example of the switching unit 60.

Hereinafter, an embodiment in which the ultrasound diagnostic apparatus management system is applied to an ultrasound diagnostic system will be described with reference to FIG. 8.

Figure 8:
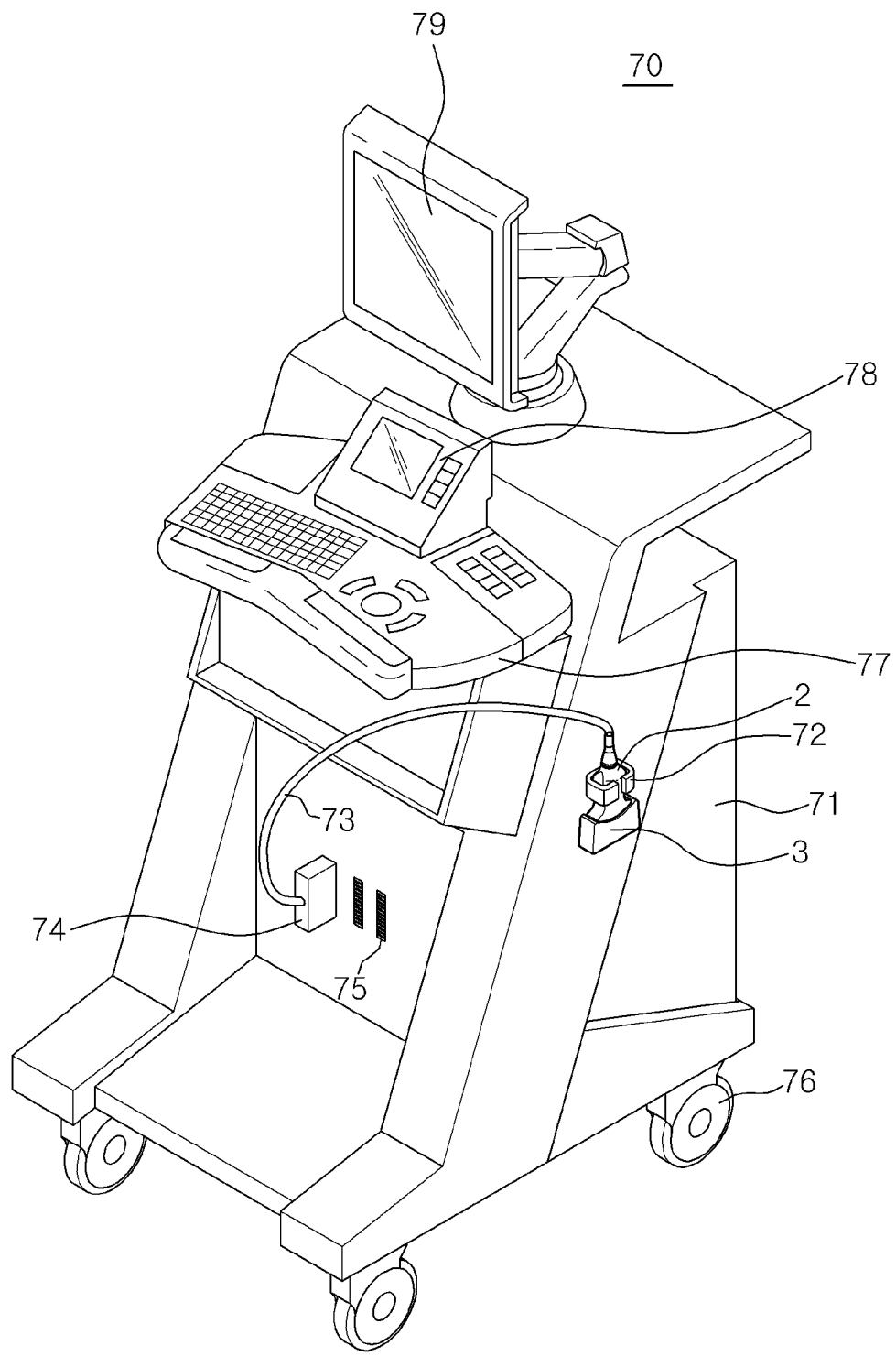
FIG. 8 is a perspective view of the ultrasound diagnostic apparatus management system applied to an ultrasound diagnostic system according to the embodiment.

FIG. 8 illustrates the ultrasound diagnostic apparatus management system applied to the ultrasound diagnostic system according to the embodiment.

An ultrasound diagnostic system 70 may include a main body 71, the ultrasound diagnosis unit 2, an input unit 77, the rearrangement unit 3, a sub-display unit 78, and a main display unit 79.

The main body 71 may accommodate a transmission signal generating unit of the ultrasound diagnostic system 70. When an ultrasound diagnosis command is input by an inspector, the transmission signal generating unit may generate a transmission signal and deliver the signal to the ultrasound diagnosis unit 2.

At least one female connector 75 may be provided in a side of the main body 71. A male connector 74 connected to a cable 73 may be physically coupled to the female connector 75. The transmission signal generated by the transmission signal generating unit may be transmitted to the ultrasound diagnosis unit 2 through the cable 73 and the male connector 74 connected to the female connector 75 of the main body 71.

Meanwhile, a plurality of castors 76 for moving the ultrasound diagnostic system 70 may be provided below the main body 71. The plurality of castors 76 enable the ultrasound diagnostic system 70 to be fixed at a specific place or to move in a specific direction.

The ultrasound diagnosis unit 2 is a unit that comes in contact with a body surface of the subject, and may transmit and receive an ultrasound. Specifically, the ultrasound diagnosis unit 2 converts a generation signal received from the main body 71 into an ultrasound signal, radiates the converted ultrasound signal onto an inside of a body of the subject, receives an ultrasound echo signal reflected from a specific region inside the body of the subject, and transmits the signal to the main body 71.

For this purpose, a plurality of acoustic modules configured to generate an ultrasound according to an electrical signal may be provided in a terminal of a side of the ultrasound diagnosis unit 2.

The acoustic module may generate an ultrasound according to applied AC power. Specifically, the AC power may be provided from a power supply device outside the acoustic module or an internal power storage device. The piezoelectric layer 32 of the acoustic module may vibrate according to the provided AC power and generate an ultrasound.

The plurality of acoustic modules may be arranged in a straight line (linear array) or in a curved line (convex array). A cover covering the acoustic module may be provided above the acoustic module.

The cable 73 is connected to a terminal of the other side of the ultrasound diagnosis unit 2. The male connector 74 may be connected to a terminal of the cable 73. The male connector 74 may be physically coupled to the female connector 75 of the main body 71.

The input unit 77 is a unit that can receive a command related to an operation of the ultrasound diagnostic system 70. For example, a mode selecting command such as an A-mode (amplitude mode), a B-mode (brightness mode), and an M-mode (motion mode), an ultrasound diagnosis starting command, and the like may be received through the input unit 77. The command input through the input unit 77 may be transmitted to the main body 71 via wired or wireless communication.

The input unit 77 may include at least one of a touchpad, a keyboard, a foot switch, and a foot pedal. The touchpad and the keyboard may be implemented in the form of hardware and located above the main body 71. The keyboard may include at least one of a switch, a key, a wheel, a joystick, a trackball, and a knob. As another example, the keyboard may also be implemented in the form of software such as a graphic user interface. In this case, the keyboard may be displayed through the sub-display unit 78 or the main display unit 79. The foot switch or the foot pedal may be provided below the main body 71, and an operator may control operations of the ultrasound diagnostic system 70 using the foot pedal.

A diagnosis unit holder 72 for mounting the ultrasound diagnosis unit 2 may be provided in the vicinity of the input unit 77. When the ultrasound diagnostic system 70 is not used, the inspector may mount and keep the ultrasound diagnosis unit 2 on the diagnosis unit holder 72. While FIG. 8 illustrates a case in which a single diagnosis unit holder 72 is provided in the vicinity of the input unit 77, the present invention is not limited thereto. Positions and the number of diagnosis unit holders 72 may be variously changed according to an entire design of the ultrasound diagnostic system 70 or designs or positions of some components.

The rearrangement unit 3 may be positioned below the diagnosis unit holder 72 on which the ultrasound diagnosis unit 2 is mounted. When the user inputs the input signal for rearrangement through the input unit 77, the rearrangement unit 3 may apply the voltage for rearrangement to the acoustic module of the diagnosis unit 2 that is fixed by the diagnosis unit holder 72 and docked in the rearrangement unit 3, and rearrange the piezoelectric layer 32 of the acoustic module. In this manner, when the user does not perform ultrasound diagnosis and keeps the ultrasound diagnosis unit 2 in the diagnosis unit holder 72, the capacitance of the acoustic module is measured and the acoustic module is rearranged when rearrangement is necessary. As a result, it is possible to improve degraded performance of the ultrasound diagnosis unit 2.

The sub-display unit 78 may be provided in the main body 71. FIG. 8 illustrates a case in which the sub-display unit 78 is provided above the input unit 77. The sub-display unit 78 may be implemented as a cathode ray tube (CRT), a liquid crystal display (LCD), and the like. The sub-display unit 78 may display an instruction, a menu necessary for ultrasound diagnosis, and the like.

The main display unit 79 may be provided in the main body 71. FIG. 8 illustrates a case in which the main display unit 79 is provided above the sub-display unit 78. The main display unit 79 may be implemented as the CRT or the LCD. The main display unit 79 may display an ultrasound image obtained in an ultrasound diagnosis process. The ultrasound image displayed through the main display unit 79 may include at least one of a 2D black and white ultrasound image, a 2D color ultrasound image, a 3D black and white ultrasound image, and a 3D color ultrasound image.

FIG. 8 exemplifies a case in which both the sub-display unit 78 and the main display unit 79 are provided in the ultrasound diagnostic system 70. However, in some cases, the sub-display unit 78 may not be provided. In this case, applications, menus, and the like displayed through the sub-display unit 78 may be displayed through the main display unit 79.

In addition, at least one of the sub-display unit 78 and the main display unit 79 may also be detachable from the main body 71.

Hereinafter, a method of rearranging the acoustic module when the diagnosis unit is docked in the rearrangement unit 3 by measuring a capacitance of the acoustic module according to the embodiment will be described with reference to FIG. 9.

Figure 9:
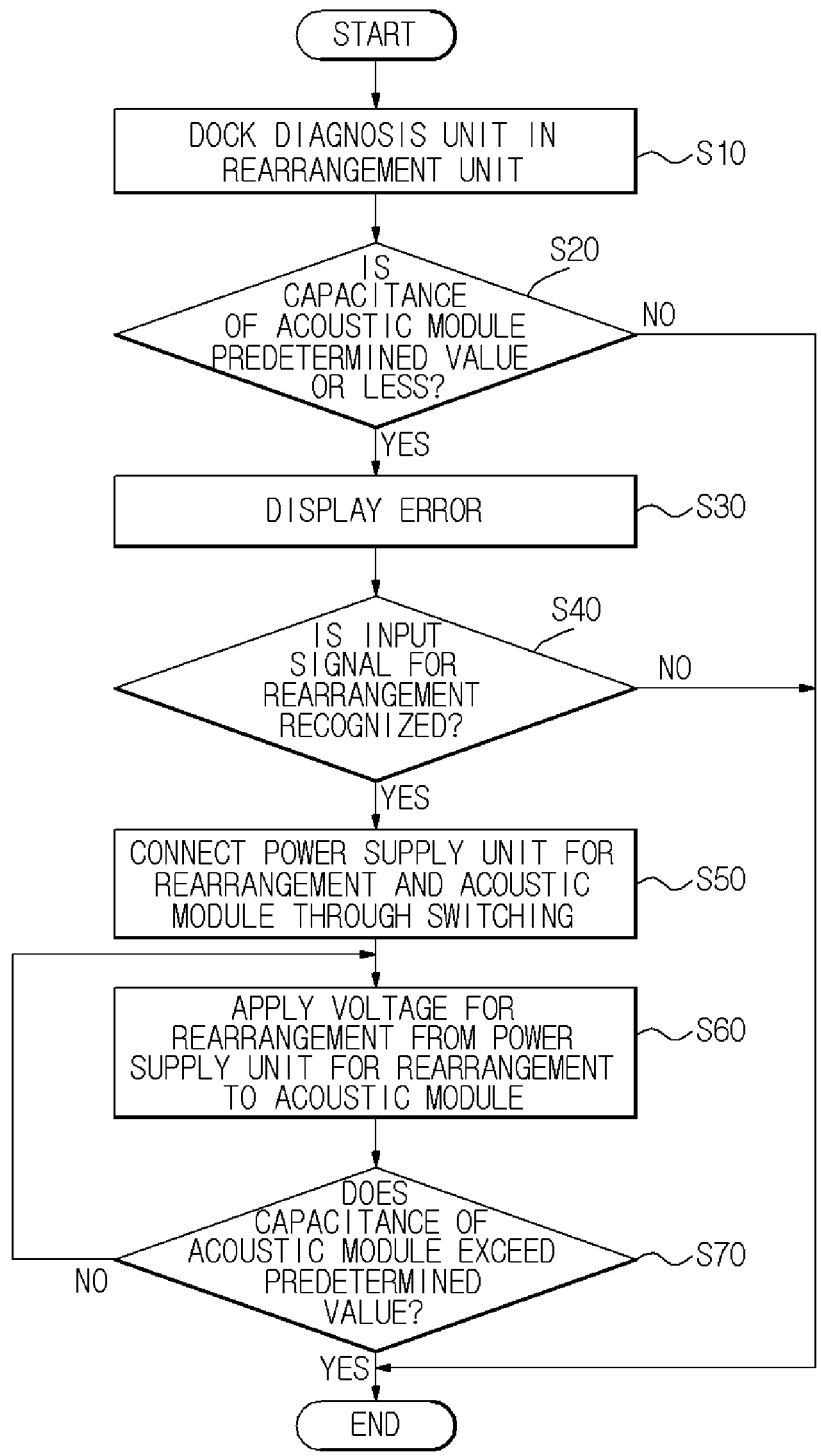
FIG. 9 is a flowchart illustrating a method of applying a voltage for rearrangement from a power supply unit for rearrangement to an acoustic module depending on a capacitance of the acoustic module according to an embodiment.

FIG. 9 illustrates a method of applying, by the power supply unit for rearrangement, a voltage for rearrangement to the acoustic module depending on the capacitance of the acoustic module according to the embodiment.

First, when the user inserts the diagnosis unit into the rearrangement unit in a set direction and the diagnosis unit is docked in the rearrangement unit (S10), the detecting unit 16 may measure a capacitance of the acoustic module and determine whether a value thereof is a predetermined value or less (S20). In this case, the predetermined capacitance may vary depending on variables such as a length, a thickness, a width, and the like of the acoustic module, may have a predetermined arbitrary value in manufacturing in consideration of a size and the like of the manufactured acoustic module, or may have a value input by the user through an input device.

When the measured capacitance of the acoustic module is not a predetermined value or less, it is determined that performance of the acoustic module is in a normal state, and the rearrangement operation may be terminated. On the other hand, when the measured capacitance of the acoustic module is a predetermined value or less, it is determined that that the performance of the acoustic module is degraded since molecule arrangement of the Perovskite crystal structure of the piezoelectric layer of the acoustic module fails to keep constant directivity due to a long-term usage or other reasons, and errors may be displayed on the display unit and the like (S30).

Then, the control unit checks whether an input signal for rearrangement is input through the input unit (S40). When the input signal for rearrangement is not recognized, the rearrangement operation may be terminated. On the other hand, when the input signal for rearrangement is recognized through the input unit, the connecting unit for rearrangement and the acoustic module may be electrically connected through switching (S50).

Then, the power supply unit for rearrangement may apply the voltage for rearrangement to the acoustic module (S60), and rearrange molecules of the piezoelectric layer such that the molecule arrangement of the Perovskite crystal structure of the piezoelectric layer of the acoustic module has constant directivity. In this case, in order to generate a strong DC electric field, a high voltage may be applied as the voltage for rearrangement. For example, a voltage of 100 [V] to 200 [V] may be applied.

Finally, even when the voltage for rearrangement is applied to the acoustic module, the detecting unit 16 measures a capacitance of the acoustic module and may determine whether a value thereof exceeds a predetermined capacitance (S70). When the capacitance of the acoustic module does not exceed a predetermined value, it is determined that rearrangement is further necessary, and then the voltage for rearrangement may be applied to the acoustic module again (S60). On the other hand, when the capacitance of the acoustic module exceeds the predetermined value, it is determined that rearrangement is completed, and then the rearrangement operation may be terminated.

In the ultrasound diagnostic apparatus management system and the method of controlling the ultrasound diagnostic apparatus management system, power for rearrangement is applied according to a state of the acoustic module of the ultrasound diagnostic apparatus. Therefore, it is possible to selectively and efficiently manage the ultrasound diagnostic apparatus.

The above description is only an example describing a technological scope of the present invention. Various changes, modifications, and replacements may be made without departing from the spirit and scope of the present invention by those skilled in the field of medical devices. Therefore, the embodiments disclosed in the above and the accompanying drawings should be considered in a descriptive sense only and not for limiting the technological scope. The technological scope of the present invention is not limited by these embodiments and the accompanying drawings. The spirit and scope of the present invention should be interpreted by the appended claims and encompass all equivalents falling within the scope of the appended claims.

What is claimed is:

1. An ultrasound diagnostic apparatus management system, comprising:
    a diagnoser including an ultrasound transducer and a connector of the diagnoser;
    a rearranger including a connector for rearrangement in which the connector of the diagnoser is docked and a power supplier for rearrangement;
    a detector configured to measure a capacitance of a piezoelectric layer of the ultrasound transducer; and
    a controller configured to control the power supplier for rearrangement to apply a voltage for rearrangement to the piezoelectric layer of the ultrasound transducer when the measured capacitance is a predetermined value or less.

2. The system according to claim 1,
    wherein the controller is configured to control the power supplier for rearrangement to apply the voltage for rearrangement to the piezoelectric layer of the ultrasound transducer until the measured capacitance exceeds a predetermined value.

3. The system according to claim 1,
    wherein the diagnoser includes:
    an ultrasound-generation-signal receiver configured to receive an ultrasound generation signal; and
    a switch configured to switch between the ultrasound-generation-signal receiver and the connector of the diagnoser.

4. The system according to claim 3,
    wherein the ultrasound-generation-signal receiver is able to wirelessly communicate.

5. The system according to claim 1,
    wherein the power supplier for rearrangement wirelessly applies the voltage for rearrangement.

6. The system according to claim 1,
    wherein the rearranger includes a cleaner configured to clean the diagnoser.

7. The system according to claim 1,
    wherein the rearranger includes a sterilizer configured to sterilize the diagnoser.

8. The system according to claim 1,
    wherein the connector of the diagnoser is plural in number and each connector has a different shape, and
    wherein the connector for rearrangement is plural in number and each connector for rearrangement has a different shape.

9. A method of controlling an ultrasound diagnostic apparatus management system, comprising:
    docking a diagnoser in a rearranger;
    measuring a capacitance of a piezoelectric layer of an ultrasound transducer in the diagnoser; and
    applying, by a power supplier for rearrangement, a voltage for rearrangement to the piezoelectric layer of the ultrasound transducer of the docked diagnoser when the measured capacitance is a predetermined value or less.

10. The method according to claim 9,
    wherein, in the applying of the voltage for rearrangement, the voltage for rearrangement is applied until the measured capacitance exceeds a predetermined value.

11. The method according to claim 9, further comprising:
    switching the ultrasound transducer connected to an ultrasound-generation-signal receiver to a connector of the diagnoser when the measured capacitance is a predetermined value or less.

12. The method according to claim 9,
    wherein, in the applying of the voltage for rearrangement, the voltage for rearrangement is wirelessly applied.

13. The method according to claim 9, further comprising:
    cleaning the diagnoser using a cleaner of the rearranger.

14. The method according to claim 9, further comprising:
    sterilizing the diagnoser using a sterilizer of the rearranger.

* * * * *